(12) United States Patent
Stroebech et al.

(10) Patent No.: US 11,077,224 B2
(45) Date of Patent: Aug. 3, 2021

(54) OSTOMY DEVICE

(71) Applicant: Coloplast A/S, Humlebaek (DK)

(72) Inventors: Esben Stroebech, Hoersholm (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 586 days.

(21) Appl. No.: 15/547,810

(22) PCT Filed: Feb. 2, 2016

(86) PCT No.: PCT/DK2016/050027
§ 371 (c)(1),
(2) Date: Aug. 1, 2017

(87) PCT Pub. No.: WO2016/124202
PCT Pub. Date: Aug. 11, 2016

(65) Prior Publication Data
US 2018/0021474 A1   Jan. 25, 2018

(30) Foreign Application Priority Data
Feb. 2, 2015 (DK) .......................... PA 2015 70057

(51) Int. Cl.
*A61L 24/04* (2006.01)
*A61F 5/448* (2006.01)
(Continued)

(52) U.S. Cl.
CPC ............ *A61L 24/043* (2013.01); *A61F 5/443* (2013.01); *A61F 5/448* (2013.01); *A61L 24/001* (2013.01); *A61L 2400/14* (2013.01)

(58) Field of Classification Search
CPC combination set(s) only.
See application file for complete search history.

(56) References Cited

U.S. PATENT DOCUMENTS

| 2,608,542 A | 8/1952 | Smith et al. |
| 2,608,543 A | 8/1952 | Wiswell |

(Continued)

FOREIGN PATENT DOCUMENTS

| AU | 07572/83 B2 | 2/2003 |
| AU | 2004203234 A1 | 9/2004 |

(Continued)

OTHER PUBLICATIONS

"3M™ Hi-Tack Transfer Adhesive", Information Sheet, Product No. 1504, published Sep. 2006.

(Continued)

*Primary Examiner* — Guy K Townsend
(74) *Attorney, Agent, or Firm* — Coloplast Corp., Coloplast A/S; Nick Baumann (57) ABSTRACT

Disclosed is an ostomy device with an adhesive wafer for attachment to a skin surface (S) of a user and a collecting bag (8) or collecting output from a stoma. The collecting bag is connected to the adhesive wafer, and the adhesive wafer has a through-going hole (6) for accommodating the stoma (7) of the user. The adhesive wafer includes a backing layer (3), a first switchable adhesive composition (2), a second absorbent adhesive composition (1), and a release liner, and the second adhesive layer has a central portion with a first thickness and an edge portion with a second thickness, the first thickness being larger than the second thickness.

13 Claims, 1 Drawing Sheet

(51) Int. Cl.
*A61L 24/00* (2006.01)
*A61F 5/443* (2006.01)

(56) References Cited

U.S. PATENT DOCUMENTS

| | | | |
|---|---|---|---|
| 3,302,647 A | 2/1967 | Marsan | |
| 3,612,053 A | 10/1971 | Pratt | |
| 4,125,522 A | 11/1978 | Becker | |
| 4,367,732 A * | 1/1983 | Poulsen | A61L 24/0094 602/56 |
| 4,614,787 A | 9/1986 | Szycher et al. | |
| 4,847,137 A | 7/1989 | Kellen et al. | |
| 5,013,307 A * | 5/1991 | Broida | A61F 5/445 604/332 |
| 5,030,665 A | 7/1991 | Lee et al. | |
| 5,087,686 A | 2/1992 | Ansell et al. | |
| 5,124,076 A | 6/1992 | Smuckler | |
| 5,256,447 A | 10/1993 | Oxman et al. | |
| 5,387,450 A | 2/1995 | Stewart | |
| 5,412,035 A | 5/1995 | Schmitt et al. | |
| 5,472,991 A | 12/1995 | Schmitt et al. | |
| 5,486,158 A * | 1/1996 | Samuelsen | A61F 13/0213 602/46 |
| 5,591,447 A * | 1/1997 | Jensen | A61F 13/023 424/443 |
| 5,622,711 A | 4/1997 | Chen | |
| 5,633,010 A | 5/1997 | Chen | |
| 5,643,187 A | 7/1997 | Naestoft et al. | |
| 5,648,167 A | 7/1997 | Peck | |
| 5,648,425 A | 7/1997 | Everaerts et al. | |
| 5,695,837 A | 12/1997 | Everaerts et al. | |
| 5,714,225 A | 2/1998 | Hansen et al. | |
| 5,714,305 A | 2/1998 | Teng et al. | |
| 5,722,965 A * | 3/1998 | Kuczynski | A61F 5/448 604/344 |
| 5,800,685 A | 9/1998 | Perrault | |
| 5,814,031 A | 9/1998 | Mooney et al. | |
| 5,853,864 A | 12/1998 | Bunnelle | |
| 5,895,623 A | 4/1999 | Trokhan et al. | |
| 5,922,470 A | 7/1999 | Bracken et al. | |
| 6,060,159 A | 5/2000 | Delgado et al. | |
| 6,068,852 A | 5/2000 | Shah | |
| 6,071,268 A * | 6/2000 | Wagner | A61F 5/443 604/332 |
| 6,143,798 A | 11/2000 | Jensen et al. | |
| 6,171,289 B1 * | 1/2001 | Millot | A61F 5/443 604/336 |
| 6,184,264 B1 | 2/2001 | Webster | |
| 6,231,872 B1 | 5/2001 | Mooney et al. | |
| 6,342,561 B1 | 1/2002 | Engel et al. | |
| 6,399,672 B1 | 6/2002 | Ceska et al. | |
| 6,451,883 B1 | 9/2002 | Chen et al. | |
| 6,589,222 B1 * | 7/2003 | Olsen | A61F 5/443 604/336 |
| 6,602,232 B1 * | 8/2003 | Keyes | A61F 5/443 604/338 |
| 6,610,762 B1 | 8/2003 | Webster | |
| 6,624,273 B1 | 9/2003 | Everaerts et al. | |
| 6,635,704 B2 | 10/2003 | Engel et al. | |
| 6,718,212 B2 | 4/2004 | Parry et al. | |
| 6,855,386 B1 | 2/2005 | Daniels et al. | |
| 6,966,901 B2 * | 11/2005 | Leisner | A61F 5/448 604/337 |
| 7,067,601 B2 | 6/2006 | Woods et al. | |
| 7,147,742 B2 | 12/2006 | Kirsten | |
| 7,214,217 B2 * | 5/2007 | Pedersen | A61F 5/441 604/332 |
| 7,235,593 B2 | 6/2007 | Crivello | |
| 7,259,190 B2 | 8/2007 | Lykke | |
| 7,396,976 B2 | 7/2008 | Hurwitz et al. | |
| 7,399,800 B2 | 7/2008 | Burch | |
| 7,479,530 B2 | 1/2009 | Hughes et al. | |
| 7,501,133 B2 | 3/2009 | McNally-Heintzelman et al. | |
| 7,722,586 B2 * | 5/2010 | Mullejans | A61F 5/448 604/342 |
| 7,767,752 B2 | 8/2010 | Kim et al. | |
| 7,836,914 B2 | 11/2010 | Drott et al. | |
| 7,879,942 B2 | 2/2011 | O'Brien et al. | |
| 7,893,179 B2 | 2/2011 | Anderson et al. | |
| 7,901,532 B2 * | 3/2011 | Bain | B60J 10/70 156/247 |
| 7,947,366 B2 | 5/2011 | Ishiwatari et al. | |
| 7,968,188 B2 | 6/2011 | Gilbert | |
| 8,044,234 B2 | 10/2011 | Hadba et al. | |
| 8,101,042 B2 | 1/2012 | Gantner et al. | |
| 8,319,003 B2 * | 11/2012 | Olsen | A61F 5/443 602/54 |
| 8,329,976 B2 | 12/2012 | Freiding et al. | |
| 8,404,921 B2 | 3/2013 | Lee et al. | |
| 8,409,158 B2 * | 4/2013 | Edvardsen | A61F 5/443 604/318 |
| 8,409,703 B2 | 4/2013 | Burch | |
| 8,410,332 B2 | 4/2013 | Burton et al. | |
| 8,414,987 B2 | 4/2013 | Guo et al. | |
| 8,439,884 B2 | 5/2013 | Fabo et al. | |
| 8,507,081 B2 | 8/2013 | Strobech et al. | |
| 8,545,468 B2 * | 10/2013 | Fabo | A61L 24/046 604/338 |
| 8,557,378 B2 | 10/2013 | Yamanaka et al. | |
| 8,664,326 B2 | 3/2014 | Lee et al. | |
| 8,679,082 B2 | 3/2014 | Bach et al. | |
| 8,690,849 B2 * | 4/2014 | Bach | A61F 5/445 604/344 |
| 8,697,932 B2 * | 4/2014 | Tunius | C09J 133/08 602/54 |
| 8,728,047 B2 | 5/2014 | Ciok | |
| 8,758,316 B2 * | 6/2014 | Mullejans | A61F 5/445 604/333 |
| 8,802,806 B2 | 8/2014 | Lam et al. | |
| 8,828,181 B2 | 9/2014 | Burch | |
| 8,864,493 B2 | 10/2014 | Leslie-Martin et al. | |
| 8,951,237 B2 | 2/2015 | Nordby et al. | |
| 8,957,277 B2 | 2/2015 | Carty et al. | |
| 9,023,249 B2 | 5/2015 | Fathi et al. | |
| 9,034,941 B2 | 5/2015 | Nielsen et al. | |
| 9,040,076 B2 * | 5/2015 | Tunius | C09J 175/16 424/445 |
| 9,066,812 B2 * | 6/2015 | Edvardsen | A61F 5/4404 |
| 9,622,903 B2 * | 4/2017 | Israelson | A61F 5/448 |
| 9,724,227 B2 * | 8/2017 | Hansen | A61L 24/001 |
| 9,999,535 B2 * | 6/2018 | Lam | A61F 5/4404 |
| 10,322,026 B2 * | 6/2019 | Hansen | A61F 5/449 |
| 2002/0165477 A1 * | 11/2002 | Dunshee | A61F 13/0203 602/58 |
| 2003/0093042 A1 * | 5/2003 | Leisner | A61F 5/448 604/337 |
| 2004/0121120 A1 | 6/2004 | Gray et al. | |
| 2004/0151902 A1 * | 8/2004 | Ansell | C08F 277/00 428/343 |
| 2004/0242770 A1 | 12/2004 | Feldstein et al. | |
| 2005/0112182 A1 | 5/2005 | Minami et al. | |
| 2005/0233149 A1 * | 10/2005 | Ansell | C08F 277/00 428/420 |
| 2006/0052478 A1 | 3/2006 | Madsen et al. | |
| 2006/0100299 A1 | 5/2006 | Malik et al. | |
| 2006/0200101 A1 * | 9/2006 | Mullejans | A61F 5/445 604/339 |
| 2006/0228318 A1 | 10/2006 | Fabo | |
| 2006/0235149 A1 | 10/2006 | Burch | |
| 2007/0004896 A1 | 1/2007 | Ito et al. | |
| 2007/0092733 A1 | 4/2007 | Yang et al. | |
| 2007/0123832 A1 | 5/2007 | Cline et al. | |
| 2007/0191517 A1 | 8/2007 | Chun et al. | |
| 2007/0196454 A1 | 8/2007 | Stockman et al. | |
| 2007/0202245 A1 | 8/2007 | Gantner et al. | |
| 2007/0249484 A1 | 10/2007 | Benkhoff et al. | |
| 2007/0255402 A1 | 11/2007 | Moore et al. | |
| 2007/0282284 A1 * | 12/2007 | Mullejans | A61F 5/448 604/333 |
| 2008/0097361 A1 * | 4/2008 | Fabo | A61F 5/443 604/338 |
| 2009/0012208 A1 | 1/2009 | Madsen et al. | |
| 2009/0171258 A1 | 7/2009 | Stroebeck et al. | |

(56) References Cited

U.S. PATENT DOCUMENTS

| | | | |
|---|---|---|---|
| 2009/0312685 A1* | 12/2009 | Olsen | A61F 13/0269 602/54 |
| 2010/0113999 A1 | 5/2010 | Lam et al. | |
| 2010/0114044 A1* | 5/2010 | Cramer | A61F 5/443 604/332 |
| 2010/0168633 A1 | 7/2010 | Bougherara et al. | |
| 2010/0191201 A1* | 7/2010 | Bach | A61L 24/043 604/336 |
| 2010/0191204 A1* | 7/2010 | Bach | A61F 5/443 604/344 |
| 2010/0198176 A1* | 8/2010 | Stroebech | A61L 24/001 604/344 |
| 2010/0204556 A1 | 8/2010 | Blakley et al. | |
| 2010/0204664 A1* | 8/2010 | Bach | A61F 5/443 604/344 |
| 2010/0204665 A1* | 8/2010 | Stroebech | A61F 5/443 604/344 |
| 2010/0255239 A1* | 10/2010 | Hammond | B32B 7/12 428/41.5 |
| 2010/0267302 A1 | 10/2010 | Kantner et al. | |
| 2010/0294344 A1 | 11/2010 | Huang | |
| 2011/0034890 A1* | 2/2011 | Stroebech | A61L 24/001 604/336 |
| 2011/0045056 A1 | 2/2011 | Munro et al. | |
| 2011/0086077 A1 | 4/2011 | McCrea et al. | |
| 2011/0098665 A1 | 4/2011 | Bach et al. | |
| 2011/0118363 A1 | 5/2011 | Jensen et al. | |
| 2011/0123800 A1 | 5/2011 | Sherman et al. | |
| 2011/0142907 A1 | 6/2011 | Marchitto et al. | |
| 2011/0177329 A1 | 7/2011 | Xia et al. | |
| 2011/0218507 A1* | 9/2011 | Andersen | A61F 5/445 604/338 |
| 2011/0224593 A1* | 9/2011 | Tunius | C09J 133/08 602/54 |
| 2011/0251542 A1 | 10/2011 | Buus et al. | |
| 2011/0278797 A1 | 11/2011 | Moore | |
| 2012/0029455 A1 | 2/2012 | Perez-Foullerat et al. | |
| 2012/0100039 A1 | 4/2012 | Appeaning et al. | |
| 2012/0100326 A1 | 4/2012 | Sherman et al. | |
| 2012/0123220 A1* | 5/2012 | Iyer | C09J 7/22 600/300 |
| 2012/0135225 A1 | 5/2012 | Colas et al. | |
| 2012/0143154 A1* | 6/2012 | Edvardsen | A61F 5/4404 604/318 |
| 2012/0143155 A1* | 6/2012 | Edvardsen | A61F 5/443 604/318 |
| 2012/0302844 A1 | 11/2012 | Schnidrig et al. | |
| 2012/0315601 A1 | 12/2012 | Shchori et al. | |
| 2012/0321819 A1 | 12/2012 | Kim et al. | |
| 2013/0004749 A1 | 1/2013 | Hao et al. | |
| 2013/0017246 A1* | 1/2013 | Tunius | C09J 7/38 424/445 |
| 2013/0041042 A1 | 2/2013 | Boyden, Jr. | |
| 2013/0089581 A1 | 4/2013 | Nielsen et al. | |
| 2013/0102947 A1 | 4/2013 | Auguste | |
| 2013/0123678 A1* | 5/2013 | Carty | A61F 13/0253 602/54 |
| 2013/0133532 A1 | 5/2013 | Kian et al. | |
| 2013/0138065 A1* | 5/2013 | Buus | A61F 5/443 604/344 |
| 2013/0138068 A1 | 5/2013 | Hu et al. | |
| 2013/0158151 A1 | 6/2013 | Nielsen et al. | |
| 2013/0165838 A1 | 6/2013 | Auguste et al. | |
| 2013/0226116 A1* | 8/2013 | Edvardsen | A61F 5/445 604/338 |
| 2013/0226117 A1* | 8/2013 | Hansen | A61L 24/046 604/338 |
| 2013/0274696 A1* | 10/2013 | Lam | A61F 5/443 604/332 |
| 2013/0288052 A1 | 10/2013 | Tapio et al. | |
| 2013/0337260 A1 | 12/2013 | Tapio et al. | |
| 2014/0031734 A1 | 1/2014 | Saxena et al. | |
| 2014/0034231 A1 | 2/2014 | Schubert et al. | |
| 2014/0114265 A1* | 4/2014 | Israelson | A61F 5/443 604/342 |
| 2014/0114268 A1* | 4/2014 | Auguste | A61F 13/0213 604/368 |
| 2014/0128826 A1* | 5/2014 | Klein | A61F 5/443 604/344 |
| 2014/0163496 A1 | 6/2014 | Grum-Schwensen et al. | |
| 2014/0171538 A1 | 6/2014 | Daniels et al. | |
| 2014/0234584 A1 | 8/2014 | Hyde et al. | |
| 2014/0348896 A1 | 11/2014 | Karp et al. | |
| 2014/0358104 A1* | 12/2014 | Tse | C09J 183/10 604/372 |
| 2015/0018790 A1* | 1/2015 | Lam | A61F 5/4404 604/344 |
| 2015/0030839 A1 | 1/2015 | Satrijo et al. | |
| 2015/0190983 A1 | 7/2015 | Caicedo-Carvajal et al. | |
| 2017/0028098 A1* | 2/2017 | Pearce | A61L 24/046 602/56 |
| 2017/0239384 A1 | 8/2017 | Lam et al. | |
| 2018/0008451 A1 | 1/2018 | Stroebech | |
| 2018/0021474 A1* | 1/2018 | Stroebech | A61F 5/443 604/336 |
| 2018/0116859 A1 | 5/2018 | Strbech et al. | |
| 2019/0117824 A1 | 4/2019 | Hansen et al. | |

FOREIGN PATENT DOCUMENTS

| | | |
|---|---|---|
| CN | 1073857 A | 7/1993 |
| CN | 1199342 A | 11/1998 |
| CN | 1258208 A | 6/2000 |
| CN | 2430135 Y | 5/2001 |
| CN | 102215790 A | 10/2011 |
| CN | 102413797 A | 4/2012 |
| DE | 102008023798 A1 | 11/2009 |
| DE | 102012208597 A1 | 11/2013 |
| EP | 0135231 A1 | 3/1985 |
| EP | 0300620 A1 | 1/1989 |
| EP | 0522250 A1 | 1/1993 |
| EP | 2012718 A1 | 1/2009 |
| EP | 2305187 A2 | 4/2011 |
| EP | 2371920 A1 | 10/2011 |
| EP | 2372920 A2 | 10/2011 |
| EP | 2654633 A1 | 10/2013 |
| FR | 2629833 A1 | 10/1989 |
| GB | 1050070 A | 1/1970 |
| GB | 2230017 A | 10/1990 |
| GB | 2283916 A1 | 5/1995 |
| JP | 07-275282 A | 10/1995 |
| JP | 2001-514051 A | 9/2001 |
| JP | 2005-118564 A | 5/2005 |
| JP | 2007-231095 A | 9/2007 |
| JP | 2008-073443 A | 4/2008 |
| JP | 2010-532183 A | 10/2010 |
| JP | 2012512285 A | 5/2012 |
| JP | 2012530546 A | 12/2012 |
| JP | 2013527860 A | 7/2013 |
| RU | 2005113227 A | 10/2005 |
| RU | 2341539 C2 | 12/2008 |
| WO | 90/13420 A1 | 11/1990 |
| WO | 97/06836 A2 | 2/1997 |
| WO | 98/26811 A2 | 6/1998 |
| WO | 98/53771 A1 | 12/1998 |
| WO | 98/55057 A1 | 12/1998 |
| WO | 99/18136 A1 | 4/1999 |
| WO | 99/29273 A1 | 6/1999 |
| WO | 99/36017 A1 | 7/1999 |
| WO | 00/14131 A1 | 3/2000 |
| WO | 00/61051 A1 | 10/2000 |
| WO | 00/61692 A1 | 10/2000 |
| WO | 01/85077 A1 | 11/2001 |
| WO | 03/61720 A1 | 7/2003 |
| WO | 2004/108175 A1 | 12/2004 |
| WO | 2005/013873 A1 | 2/2005 |
| WO | 2006/038025 A1 | 4/2006 |
| WO | 2007082538 A1 | 7/2007 |
| WO | 07121744 A1 | 11/2007 |
| WO | 2009000273 A1 | 12/2008 |
| WO | 2009006900 A1 | 1/2009 |

(56) References Cited

FOREIGN PATENT DOCUMENTS

| WO | 2009006901 A1 | 1/2009 | | |
|---|---|---|---|---|
| WO | 2009006902 A1 | 1/2009 | | |
| WO | WO200900690 A1 * | 1/2009 | ............ | A61F 5/445 |
| WO | WO-2009006900 A1 * | 1/2009 | ............ | A61L 24/04 |
| WO | 2009087877 A1 | 7/2009 | | |
| WO | 2010/034998 A1 | 4/2010 | | |
| WO | 2010069333 A1 | 6/2010 | | |
| WO | 2010148182 A1 | 12/2010 | | |
| WO | 2011/063082 A2 | 5/2011 | | |
| WO | 2011121303 A1 | 10/2011 | | |
| WO | 2012/048128 A2 | 4/2012 | | |
| WO | 12083964 A1 | 6/2012 | | |
| WO | 2012/097199 A2 | 7/2012 | | |
| WO | 2013/022898 A1 | 2/2013 | | |
| WO | 2013066401 A1 | 5/2013 | | |
| WO | 13096530 A1 | 6/2013 | | |
| WO | 2013/148506 A1 | 10/2013 | | |
| WO | 2014/028024 A1 | 2/2014 | | |
| WO | 2014/066195 A1 | 5/2014 | | |
| WO | 2014/080954 A1 | 5/2014 | | |
| WO | 2014/093246 A1 | 6/2014 | | |
| WO | 2014/202935 A1 | 12/2014 | | |
| WO | 2015/132551 A1 | 9/2015 | | |
| WO | 2016/055075 A1 | 4/2016 | | |
| WO | 2016/124202 A1 | 8/2016 | | |
| WO | 2016/124203 A1 | 8/2016 | | |

OTHER PUBLICATIONS

"A permeable pressure sensitive adhesive", Danish patent application PA 2007 01003 filed by Coloplast A/S, Jul. 2007.

International Preliminary Report on Patentability received for PCT Patent Application No. PCT/DK2016/050027, dated Jan. 24, 2017, 10 pages.

International Preliminary Report on Patentability received for PCT Patent Application No. PCT/DK2016/050028, dated Jan. 5, 2017, 13 pages.

International Preliminary Report on Patentability received for PCT Patent Application No. PCT/DK2016/050099, dated Jul. 24, 2017, 14 pages.

International Preliminary Report on Patentability received for PCT Patent Application No. PCT/DK2017/050112, dated Mar. 20, 2018, 14 pages.

International Search Report and Written Opinion received for PCT Patent Application No. PCT/DK2016/050027, dated Apr. 20, 2016, 10 pages.

International Search Report and Written Opinion received for PCT Patent Application No. PCT/DK2016/050028, dated Apr. 20, 2016, 11 pages.

International Search Report and Written Opinion received for PCT Patent Application No. PCT/DK2016/050099, dated Jul. 27, 2016, 11 pages.

International Search Report and Written Opinion received for PCT Patent Application No. PCT/DK2017/050112, dated Jun. 9, 2017, 12 pages.

Dumitriu, S. "Polymeric Biomaterials, Revised and Expanded", 2001, CRC Press, p. 710.

Santini et al., "Photoinitiators in dentistry: a review", Primary Dental Journal, vol. 2, No. 4, p. 30-34, Oct. 2013.

Neumann et al., "The effect of the mixtures of photoinitiators in polymerization efficiencies", Journal of Applied Polymer Science, vol. 112, p. 129-134, 2008.

Czech et al., "UV-crosslinkable acrylic pressure-sensitive adhesives for industrial application", Polym. Bull., vol. 69, p. 71-80, 2012.

* cited by examiner

OSTOMY DEVICE

Disclosed is an ostomy device with an adhesive wafer for attachment to a skin surface of a user and a collecting bag connected to the adhesive wafer. The adhesive wafer includes a backing layer, a switchable adhesive composition, an absorbent adhesive composition, and a release liner.

BACKGROUND

In connection with surgery for a number of diseases in the gastro-intestinal tract, one of the consequences in many cases is that the patient is left with an abdominal stoma, such as a colostomy, an ileostomy or a urostomy, in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time. Ostomy appliances are typically attached to the skin of the ostomy user by means of an adhesive wafer on the ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Embodiments provide an ostomy device comprising an adhesive wafer for attachment to a skin surface of a user, and a collecting bag for collecting output from a stoma, the bag being connected to the adhesive wafer; the adhesive wafer having a through-going hole for accommodating the stoma of the user; and the adhesive wafer comprising a backing layer, a first switchable adhesive layer, a second adhesive layer, and a release liner, the first adhesive layer at least partly overlying a second adhesive layer, wherein the second adhesive layer has a central portion with a first thickness and an outer edge portion with a second thickness, the first thickness being larger than the second thickness.

In embodiments, the adhesive wafer will have a proximal ("skin-facing") surface, which faces the skin of the user during use, and a distal ("non-skin-facing") surface, which faces away from the user's skin during use. Before use, the proximal surface of the adhesive wafer can be covered by a release liner, which is releasably attached to the adhesive. The release liner can be removed by the user immediately prior to application of the adhesive wafer to the skin. Both before and during use, the distal surface of the adhesive wafer can be made up of a backing layer, which can be used to attach the collecting bag to the adhesive wafer, for instance by welding. As such, the adhesive wafer may comprise a distal backing layer and a proximal release liner, with the first switchable adhesive composition and the second absorbent adhesive composition located between the backing layer and the release liner.

The adhesive wafer includes a first switchable adhesive composition. Switchable means that the adhesive can be switched between at least two different states with different properties.

The switch is the transition from one state to another state of a switchable composition. The duration of the switch will vary depending on, e.g., the nature of the switch initiator and the method of activation of the switch initiator. Generally, the switch will be a gradual process with a gradual change of physical properties of the material from one state to another state. In some instances, the switch will be very fast and the physical properties will change very quickly, e.g. within seconds, to those of the second state. In other instances, the switch will be slower and the change in properties will happen gradually over a period of, e.g., several minutes or even hours.

In embodiments, the switchable adhesive composition can be switched from a tacky state to a non-tacky or low-tack state in which the switched adhesive has a reduced peel strength relative to the peel strength of the adhesive before switching.

Since the switchable adhesive composition can be switched to a non-tacky or low-tack state, it can initially be provided in a high-tack state with a tack that would otherwise not be suitable for use on skin because it would be too difficult or too painful to remove. In other words, the pre-switch tack can be very high because it is not required that the adhesive can be removed again from the skin in the pre-switch state. In this manner, the switchable adhesive composition can be made to have a pre-switch application state, in which the properties are suitable for application to the skin of the user, and a post-switch removal state, in which the properties are suitable for removing the adhesive from the skin.

Recognizing that the expression "low-tack" is a relative term, it will be defined here as meaning the condition of minimum tackiness which the adhesive reaches after switching from its tacky state. The reduction in peel force may be as great as 100% or as little as 30%. In embodiments, the reduction in peel force is 30-40%, 30-50%, 30-60%, 30-70%, 30-80%, 30-90%, 30-100%, 40-50%, 40-60%, 40-70%, 40-80%, 40-90%, 40-100%, 50-60%, 50-70%, 50-80%, 50-90%, 50-100%, 60-70%, 60-80%, 60-90%, 60-100%, 70-80%, 70-90%, 70-100%, 80-90%, 80-100%, or 90-100%. In embodiments, the reduction in peel force is at least 50%.

The adhesive wafer includes a second adhesive composition. The second adhesive composition may be an absorbent adhesive. The absorbent adhesive composition is capable of absorbing moisture. The purpose of having an absorbent adhesive composition as a part of an ostomy device is to allow the absorbent adhesive composition to absorb moisture produced by the skin and thereby prevent accumulation of moisture at the skin surface, underneath the ostomy device. Accumulation of moisture on the skin surface can lead to damage of the skin, such as maceration.

By providing an adhesive wafer having both a switchable adhesive composition and an absorbent adhesive composition, the present inventors have been able to construct an ostomy device, which can adhere quickly and strongly to the skin of the user and at the same time properly absorb moisture to prevent damage to the skin underneath the adhesive. The fast and strong adhesion to the skin effected by the switchable adhesive composition further leads to prevention of leakage of output from the ostomy.

Furthermore, when combining a switchable adhesive with an absorbent adhesive, problems may occur during detachment of the wafer. First step of removal is to switch the switchable adhesive by exposing it to light (or other stimuli). This will turn the adhesive from highly tacky to a very low tack. The second adhesive, not being switchable, maintains its tackiness to the skin. When the wafer is peeled off the skin by gripping the edge portion of the wafer (the first adhesive) and pulling, the first adhesive will come off easily, being switched into a low tack state, whereas the second adhesive still maintains good adhesion to the skin. Thus, there is a risk that the wafer will delaminate such that the first switchable adhesive will come off the skin and delaminate from the second adhesive, whereas the second absorbent adhesive may remain wholly or partially on the skin. Having the second absorbent adhesive remain attached to the skin or having residue from the second absorbent adhesive stuck to the skin after removal of the rest of the adhesive is a highly undesirable situation.

By using a switchable adhesive composition with a pre-switch high-tack state, a quick initial adherence between the adhesive and the skin of the user can take place. Such a quick and strong adhesion will, already from application of the adhesive to the skin, prevent output from leaking into the space between the skin and the adhesive. This is in contrast to some non-switchable pressure sensitive adhesives, which typically require a significant amount of time, such as 10-60 minutes, to achieve strong adhesion. By applying pressure to the pressure sensitive adhesive it is possible for the adhesive to wet and flow faster into the skin surface, hereby obtaining a large contact area and hereby increasing the adhesive power. Some current adhesive systems for attachment of ostomy device to the skin require a high or prolonged pressure from the user in order to sufficiently flow into and wet the surface of the substrate. By using a switchable adhesive with an initial high tack, neither a high pressure nor a long time is needed in order to ensure a good and enduring adhesion to the skin.

In addition to the early formation of a strong adhesive bond, the switchable adhesive also makes it possible to maintain a very strong adhesive bond during the entire period of use of the ostomy device. This is because it is not necessary to be able to remove the adhesive in the pre-switched state. Therefore, the adhesion to the skin in the pre-switched state can remain very high right up until the switch causes the adhesion to drop significantly, thus allowing easy and pain-less removal of the device.

In embodiments, the first switchable adhesive composition is in contact with the backing layer. The first switchable adhesive composition may be disposed on the backing layer or coated on the backing layer. By being in contact with the backing layer, at least part of the switchable adhesive composition is close to the distal non-skin-facing surface of the adhesive wafer. This will make it easier to effect the switch of the switchable adhesive composition, for instance by applying light to the switchable adhesive composition through the backing layer.

In embodiments, the release liner is in contact with both the first switchable adhesive composition and the second absorbent adhesive composition. The release liners covers the surface of the adhesive that is to be attached to the skin of the user. As such, the surface of the adhesive that is in contact with the release liner is also the surface that will be in contact with the skin of the user during use. By having both the first switchable adhesive composition and the second absorbent adhesive composition form part of the adhesive surface that comes into contact with the user's skin, it is ensured that both adhesives can exert their respective effects directly on the skin. In other words, both adhesive compositions will be in contact with the user's skin during use. The switchable adhesive composition can cause the rapid, strong, and enduring adhesion to the skin and the absorbent adhesive composition can ensure that moisture is effectively removed from the surface of the skin.

In embodiments, the second absorbent adhesive composition is located between the first switchable adhesive composition and the release liner. The absorbent adhesive composition can cover a part of the surface of the switchable adhesive composition on the proximal skin-facing side of the adhesive wafer. The switchable adhesive composition can cover the entire distal non-skin-facing surface of the absorbent adhesive composition. By such an arrangement, the absorbent adhesive will come into contact with the skin of the user and can thereby easily absorb moisture from the skin surface. None of the switchable adhesive will be covered on the distal non-skin-facing surface by the absorbent adhesive, thus making it easier to effect the switch by, for instance, shining light on the switchable adhesive without having to have the light pass through the absorbent adhesive.

In embodiments, the adhesive wafer has a central part adjacent to the hole for accommodating the stoma and a peripheral part adjacent to an edge of the adhesive wafer away from the hole. The second absorbent adhesive composition may be located at least in the central part of the adhesive wafer. The central part of the wafer is the part that is closer to the through-going hole in the wafer than it is to the peripheral edge of the wafer. Typically, this will represent a ring-shaped area of the adhesive wafer surrounding the hole. The central part will be the part of the wafer that is closest to the stoma during use of the ostomy device. The peripheral part is the remainder of the adhesive wafer outside the central part, i.e., the part that is closer to the peripheral edge than to the hole. Typically, the peripheral part will also be a ring-shaped area of the adhesive wafer. The absorbent adhesive may be in the entire central part of the wafer or only in part of the central part. The absorbent adhesive may extend also to the peripheral part of the adhesive wafer. By being in the central part of the adhesive wafer, the absorbent adhesive will be located close to the stoma and will thereby be close to the sensitive skin surrounding the stoma. This will allow the absorbent adhesive to absorb moisture form the sensitive skin around the stoma. Also, an absorbent adhesive may be able to swell during use as a consequence of the absorption of moisture and may thus be able to increase in volume and provide a mechanical sealing around the stoma.

In embodiments, the second absorbent adhesive composition is located only in the central part of the adhesive wafer. The absorbent adhesive composition may be located as a ring-shaped element in the central part of the adhesive wafer, thus surrounding the stoma during use.

In embodiments, the first switchable adhesive composition is located at least in the peripheral part of the adhesive wafer. The switchable adhesive composition may be in the entirety of the peripheral part or only in part of the peripheral part of the wafer. The switchable adhesive composition may extend into the central part of the wafer.

In embodiments, the releaser liner is in contact with the first switchable adhesive composition in the peripheral part of the adhesive wafer. In this manner, the switchable adhesive will be in contact with the skin at the peripheral part of the adhesive wafer during use. By having the switchable adhesive composition in the peripheral part in contact with the skin during use, a strong adhesive bond is established around the periphery of the adhesive wafer, thus making it less likely that the adhesive wafer will start to peel off due to contact with the surroundings, such as the user's clothes.

In embodiments, the releaser liner is in contact with the second absorbent adhesive composition in the central part of the adhesive wafer. In this manner, the absorbent adhesive will be in contact with the skin surrounding the stoma during use. This will allow the absorbent adhesive to absorb moisture directly from the sensitive skin surrounding the stoma, thereby preventing damage to the skin, such as maceration.

In embodiments, the backing layer is suitably elastic, i.e. it has a low modulus, enabling the adhesive construction to conform to the skin movement and provide comfort when using it. The backing layer may have a structured surface to improve the adhesion between the adhesive and the backing layer. The backing layer may be a non-woven or a non-woven-film laminate. The backing layer may be a polymer film. The backing layer may comprise polyurethane. The thickness of the backing layer is dependent on the type of backing layer used. For polymer films, such as polyurethane films, the overall thickness may be between 10 to 100 micrometers, such as between 10 to 50 micrometers, such as about 30 micrometers.

The release liner may be of any material known to be useful as a release liner for medical devices. For instance, the release liner may be in the form of a polymer film, foil, or paper, having release properties that enable the adhesive to be released easily from the liner. Such properties may be inherent in the material or the layer may be siliconized, coated with a low surface tension coating, or subjected to other appropriate surface modifications. Release liners are in general made on a mechanically stiff backing such as paper, polyethylene, polypropylene, or polyethylene terephthalate. This stiffness will support the adhesive wafer when applying the collecting device.

In embodiments, the second absorbent adhesive composition is in the form of a ring-shaped adhesive element located around the hole in the adhesive wafer and in contact with the release liner. Such a ring-shaped absorbent adhesive element could have a diameter of 30-70 mm, such as 40-70 mm, such as 50-70 mm, such as 60-70 mm. The ring-shaped adhesive element could for instance have a diameter of 30 mm, 40 mm, 50 mm, 60 mm, or 70 mm. The ring shaped element could have a width, i.e. the distance from the inner rim of the ring to the outer rim of the ring measured along the surface of the ring, of at least 10 mm, at least 20 mm, at least 30 mm, at least 40 mm, at least 50 mm, 10-20 mm, 10-30 mm, 10-50 mm, 20-30 mm, 20-40 mm, 20-50 mm, 30-40 mm, 30-50 mm, or 40-50 mm. The width of the element can be constant over the entire element or it may vary.

In embodiments, the first switchable adhesive composition extends in the entire area of the adhesive wafer. In embodiments, the first switchable adhesive composition is in the form of a ring-shaped adhesive element located at the periphery of the adhesive wafer. Such a ring-shaped switchable adhesive element could have a diameter of 50-150 mm, such as 50-120 mm, such as 50-100 mm, such as 50-75 mm. The ring-shaped adhesive element could for instance have a diameter of 50 mm, 60 mm, 70 mm, 80 mm, 90 mm, 100 mm, 120 mm, or 150 mm. The ring shaped element could have a width of at least 10 mm, at least 20 mm, at least 30 mm, at least 40 mm, at least 50 mm, at least 60 mm, at least 70 mm, at least 80 mm, at least 90 mm, at least 100 mm, 10-20 mm, 10-30 mm, 10-50 mm, 10-100 mm, 20-30 mm, 20-40 mm, 20-50 mm, 20-100 mm, 30-40 mm, 30-50 mm, 30-100 mm, 40-50 mm, 40-100 mm, or 50-100 mm. The width of the element can be constant over the entire element or it may vary.

By the term "ring-shaped" is herein understood that the adhesive defines a band circumferending the central opening. The outline of this band may be substantially circular, oval or other rounded shape. An adhesive element could also have an only roughly ring-shaped, oval, or roughly oval form. In that case, the mentioned diameters would be the maximum distance from one point on the outer edge of the element to another point on the outer edge of the element.

In embodiments, the second absorbent adhesive composition has a first thickness in the central portion, i.e. the distance from one outer surface of the adhesive to the other outer surface of the adhesive measured in a straight line perpendicular to the surface of the adhesive. In embodiments, the first thickness of the absorbent adhesive composition is at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers. The first thickness of the absorbent adhesive composition may be between 50 micrometers and 1,000 micrometers, such as 100-500 micrometers, such as 200-400 micrometers, such as 200-300 micrometers. The uniform thickness of the absorbent adhesive composition may be 50-250 micrometers, 100-250 micrometers, 250-500 micrometers, 250-750 micrometers, 500-750 micrometers, 500-1,000 micrometers, 500-1500 micrometers, 500-200 micrometers, 1000-2000 micrometers.

In embodiments, the first switchable adhesive composition has a uniform thickness. In embodiments, the uniform thickness of the absorbent adhesive composition is at least 10 micrometers, such as at least 25 micrometers, such as at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers. The uniform thickness of the absorbent adhesive composition may be between 10 micrometers and 1,000 micrometers, such as 25-500 micrometers, such as 50-500 micrometers, such as 100-500 micrometers, such as 200-400 micrometers, such as 200-300 micrometers. The uniform thickness of the absorbent adhesive composition may be 10-50 micrometers, 10-100 micrometers, 25-50 micrometers, 25-100 micrometers, 50-100 micrometers, 50-250 micrometers, 100-250 micrometers, 250-500 micrometers, 250-750 micrometers, 500-750 micrometers, 500-1,000 micrometers, 500-1500 micrometers, 500-200 micrometers, 1000-2000 micrometers.

In embodiments, the first switchable adhesive composition has a varied thickness. In embodiments, the maximum thickness of the absorbent adhesive composition is at least 10 micrometers, such as at least 25 micrometers, such as at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers. The maximum thickness of the absorbent adhesive composition may be between 10 micrometers and 1,000 micrometers, such as 25-500 micrometers, such as 50-500 micrometers, such as 100-500 micrometers, such as 200-400 micrometers, such as 200-300 micrometers. The maximum thickness of the absorbent adhesive composition may be 10-50 micrometers, 10-100 micrometers, 25-50 micrometers, 25-100 micrometers, 50-100 micrometers, 50-250 micrometers, 100-250 micrometers, 250-500 micrometers, 250-750 micrometers, 500-750 micrometers, 500-1,000 micrometers. In embodiments, the first switchable adhesive composition is thicker in the peripheral part of the adhesive wafer than in the central part of the adhesive wafer. In embodiments, a thickness of the first switchable adhesive composition in the peripheral part of the adhesive wafer is at least 120%, such as at least 150%, such as at least 200%, such as at least 250%, such as at least 500% of a thickness of the first switchable adhesive composition in the central part of the adhesive wafer.

In embodiments, the switchable adhesive composition is disposed on the backing layer and covers the entire backing layer. The absorbent adhesive composition is in the form of a ring-shaped adhesive element in the center of the adhesive wafer around the hole and on the skin-facing surface of the switchable adhesive composition. In this manner, the switchable adhesive composition will be in contact with the release liner in the periphery of the wafer and the absorbent adhesive composition will be in contact with the release liner in the center of the wafer. Both adhesives will therefore be in contact with the skin of the user during use.

In embodiments, the skin-contacting surface of the adhesive wafer is constituted by the second adhesive at the central portion of the wafer and the first adhesive at the peripheral portion of the wafer. Such construction may provide sealing and moisture handling next to the stoma and a strong attachment to the skin along the periphery, thereby decreasing the risk of rolling up of the edge portion as well as leakage.

Traditional peel tests are performed by peeling an adhesive substrate from a steel plate or other stiff substrate. However, peel from skin is quite different from steel as the skin is soft and flexible and will stretch and follow the adhesive in the pull direction, thereby distributing the forces in the substrate in a different way. So, an adhesive wafer construction may show promising results without delamination when peeled from a stiff substrate, whereas peeling the same device from skin may result in delamination.

In embodiments, a bevelled edge can be described as an adhesive layer with a thickness of the central portion of one thickness and another thickness at the edge portion. The thickness decreases over a distance thereby providing a sloping line between the central and the edge portion. This line defines an angle with the plane of the adhesive layer. The angle may be 10-60 degrees, such as 15-50 degrees, such as 20-40 degrees or even 20-30 degrees. The thickness at the edge may determine the degree of delamination.

The edge portion of the second adhesive may be bevelled. By bevelled is herein meant that in a cross-section of the edge portion it defines a sloping line from the portion of the first thickness to the portion of the second thickness. The line may be linear or curvilinear.

The edge portion of the second adhesive may be bevelled in an angle of 10 to 60 with respect to the surface of the second adhesive layer.

The second thickness of the second adhesive may be less than 300 µm. The second thickness may define a rim portion of the second adhesive layer. The lower the second thickness is, the less prone is the wafer to delaminate when removed from the skin.

In embodiments, the first switchable adhesive composition comprises curable molecules selected from the group consisting of acrylic acid esters or methacrylic acid esters of alcohols, glycols, pentaerythritol, trimethylpropane, glycerol, aliphatic epoxides, aromatic epoxides including bisphenol A epoxides, aliphatic urethanes, silicones, polyesters and polyethers.

In embodiments, the first switchable adhesive composition comprises a polymer selected from the group consisting of polyacrylates, polyurethanes, and polysilicones.

In embodiments, the first switchable adhesive composition comprises a photoinitiator. A photoinitiator makes it possible to switch the adhesive composition by activating the photoinitiator with light. Different photoinitiators have different absorption spectra and will need to be activated by light in different wavelengths. In embodiments, the first switchable adhesive composition comprises a photoinitiator reactive to visible light. This will make it possible to cause the switch of the adhesive by applying regular visible light. This is a safe and convenient method of switch, especially if the switch is to be effected by the user of the ostomy device.

In some embodiments, the light comprises visible light and/or ultraviolet (UV) light. Visible light is defined as electromagnetic radiation with a wavelength in the range 400-700 nm. Ultraviolet light is defined as electromagnetic radiation with a wavelength in the range 10-400 nm. In embodiments, the photoinitiator will be reactive to ultraviolet light.

In embodiments, the first switchable adhesive composition comprises a photoinitiator selected from the group consisting of titanocene photoinitiators; dye/co-initiator systems including thionine/triethanolamine; dye/borate salt systems; dye/peroxide systems and 1,2-diketone/co-initiator systems, including camphor-quinone/tertiary amine.

In embodiments, the switchable adhesive composition may be absorbent as described herein for the absorbent adhesive composition.

In embodiments, the switchable adhesive composition is a switchable pressure sensitive adhesive (PSA) composition. The switchable PSA may comprise a mixture, in proportions by weight, of 2% to 80% of curable molecules that are curable by free radical polymerisation, 0.05% to 10% of photoinitiator and an internal cross-linker that is cross-linkable by mechanism other than free radical polymerisation for cross linking the adhesive, the balance being base adhesive polymer and incidental constituents and the weight proportions being calculated on the basis of the dry weight of the base adhesive polymer. The PSA may have a cohesive strength of between 5 and 100 N/12.7×12.7 mm measured according to FINAT test method No. 18 The cohesive strength may be significantly higher than 30 N/12.7×12.7 mm depending on the application for which the switchable PSA is intended. Preferably, the base adhesive polymer and curable molecules are mutually soluble when dry, although good results are still obtained when the curable molecules are uniformly dispersed in the adhesive even when the adhesive and curable molecules are mutually insoluble or only partly mutually soluble when dry.

The cohesive strength of the composition is determined by controlling the cohesive strength of the adhesive polymer backbone, and this is done by partially cross-linking it.

Cross-linking can be achieved by incorporating monomers of e.g. N-methylol acrylamide, N-(iso-butoxymethylene)acrylamide, methyl acrylamidoglycolate methyl ether (all 0.5-5%) or metal chelates, e.g., acetylacetonates of Zr, Al, or Fe (up to 2% of polymer weight) into the polymer backbone which then cross-links during drying after spreading on a substrate.

Al and Ti acetylacetonates and similar compounds can also be added after the polymerization step in concentrations between 0.1 and 2% of the polymer weight and used as an internal cross-linker through utilizing carboxylic groups in the polymer backbone during the drying step.

Multi-functional isocyanates like toluene diisocyanate (TDI), trimethyl hexamethylene diisocyanate (TMDI), hexamethylene diisocyanate (HDI), or isophorane diisocyanate (IPDI), can be used to chemically inter link hydroxylic or carboxylic functions of different polymer chains, added in concentrations up to about 1% of the polymer weight.

Internal cross-linking can also be achieved between the carboxylic groups in the polymer backbone and added amino resins such as melamine, benzoguanamine, glycoluril, urea derivatives e.g. hexamethoxymethyl melamine, methoxymethyl methylol melamine, methoxymethyl ethoxymethyl benzoguanamine, tetrabutoxymethyl glycoluril, butoxymethyl methylol urea (up to 6%).

The above mentioned cross-linking can also be achieved using polycarbodiimides or multifunctional propylene imines.

It is also possible to blend one or more polymers having high cohesive strength with one or more polymers having low cohesive strength in order to achieve the desired balance.

Cross-linking is also important for effective switching and it is therefore necessary to distinguish between the type of cross-linking that is undertaken for controlling the cohesive strength of the adhesive composition and the type of cross-linking that brings about switching. In the first case, cross-linking for controlling the cohesive strength of the adhesive is effected using an internal cross-linker, i.e., a cross-linker supplied with or forming part of the adhesive polymer backbone material. In the second case, cross-linking for switching is effected by visible light or UV-induced curing of the curable molecules to form a three-dimensional polymeric network entangling the chains of the base adhesive polymer backbone, thereby reducing their mobility and free volume. Preferably the amount of base adhesive polymer present in the mixture is in the range 20% to 98% by weight, more preferably 40% to 90% by weight, and most preferably 50% to 70% by weight. Preferably the proportion of curable molecules in the mixture ranges from 2% to 80% by weight, more preferably 10% to 60% by weight, and most preferably 30% to 50% by weight. Preferably, the photoinitiator is present in the mixture in the proportions 0.1% to 5% by weight, more preferably 0.5% to 2% by weight. Preferably, the photoinitiator is also soluble in the dry mixture of adhesive and curable molecules, although it will be capable of exerting its curing initiating effect upon exposure to an activating light source if finely dispersed through the dry mixture but not dissolved in it.

The weight proportion for the base adhesive polymer is given here in terms of its dry weight and excludes any solvent which might normally be present in a commercially available bulk adhesive.

In certain embodiments, the weight proportion of base adhesive polymer is from one of the following lower endpoints (inclusive), or from one of the following upper endpoints (inclusive). The lower endpoints are 20%, 30%, 40%, 50%, 60% and 70%; the upper endpoints are 98%, 95%, 90% and 85%. In certain embodiments, the weight proportion of curable molecules is from one of the following lower endpoints (inclusive), or from one of the following upper endpoints (inclusive). The lower endpoints are 2%, 5%, 10% and 15%; the upper endpoints are 80%, 70%, 60%, 50%, 40% and 30%. In certain embodiments, the weight proportion of photoinitiator is from one of the following lower endpoints (inclusive), or from one of the following upper endpoints (inclusive). The lower endpoints are 0.05%, 0.1%, 0.2%, 0.5% and 1.0%; the upper endpoints are 10%, 5%, 4% and 3%.

The incidental constituents may be one or more of stabilizers, tackifiers, light scattering particles, fungicides, colorants, humectants, etc.

The adhesive component may be a hydrocolloid having polymeric chains extending from a core or nucleus, and the reference to the adhesive and the curable molecules being mutually soluble in each other when dry is to be understood as meaning that the curable molecules and the polymeric chains are mutually soluble in each other. Hydrocolloid-based medical dressings may be used for skin and wound treatment. When first attached to the skin, dry hydrocolloids are only slightly adherent to the skin, but quickly absorb moisture from the skin and become more tacky.

The preparation method for the switchable adhesive compositions is very simple. The adhesive component, the curable molecules (monomers and/or oligomers) and the photoinitiator are mixed, preferably stirred, together in darkness or under red light conditions for about 30 to 60 minutes, most conveniently at room temperature. The mixture also includes the internal cross-linker. The internal cross-linker may be included as part of the base adhesive, for example obtained from a commercial supplier who supplies as a stock item base adhesive with internal cross-linkers. Alternatively, the internal cross-linker may be supplied as a separate component from the base adhesive. The internal cross-linker may be added to the mixture as a solution. The adhesive component is usually supplied in solution (typically, 40% to 60% solids by weight); the solvent for the adhesive may be a suitable vehicle for dissolving the internal cross-linker. The curable molecules are usually solvent free, although some curable molecules of high viscosity may be carried in a solvent which also could act to stabilize the internal cross-linker; the photoinitiator is usually solid and the most difficult component of the system to dissolve and/or disperse.

Following completion of the mixing together, the resulting composition is spread onto, e.g., a release liner at a certain thickness—typically about 60 µm when wet—and then left to dry at room temperature for about 10 minutes. The release liner may be a polyethylene coated paper with a silicone compound chemically bound to the surface. The spread adhesive is then further dried at 80-150° C. for 3 to 10 minutes. A slightly higher temperature and a longer drying time can be used if necessary. After drying, the thickness of the spread adhesive will typically be about 30 µm.

The dried adhesive is then transferred onto a carrier film, for example, for peel strength and switching evaluation.

Alternatively, the dried adhesive may be transferred to a material for a wound dressing or an ostomy appliance, for example a web of polyethylene or polyurethane film which may optionally be perforated, or a woven or non-woven fabric.

For a medical dressing or similar application, the adhesive component may be selected from polymers capable of forming shaped bodies, thin walls or coatings. Suitable polymers are biologically and pharmaceutically compatible, hypoallergenic and insoluble in and compatible with body fluids or tissues with which the dressing is contacted.

Exemplary light transmitting materials for carrying the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated poly-ethylene, polyvinyl chloride, vinyl chloride-vinyl acetate copolymer, cross-linked polymethacrylate polymers (hydrogel), polyvinylidene chloride, poly(ethylene terephthalate), butyl rubber, epichlorohydrin rubbers, ethylenevinyl alcohol copolymers, ethylenevinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoro-ethylene; and the like.

The adhesives may be water-soluble, but will most often be soluble in, and hence commercially supplied as solutions in, organic solvents such as ethyl acetate, hexane, toluene, acetone etc. Preferred adhesives are polyacrylates, polyurethanes and polysilicones. Especially preferred are polyacrylates. By the term polyacrylates is meant acrylate, methacrylate and acrylate copolymer adhesives. Indeed acrylate copolymer adhesives are most preferred, e.g. alkyl acrylate copolymers. The most commonly used monomers in polyacrylates are butyl acrylate, ethylhexyl acrylate, hydroxyethyl acrylate and acrylic acid. They may be used singly or in a mixture, their relative proportions in the mixture being selected depending on the water penetration rate, viscoelastic properties, Tg, etc., that it is desired to achieve.

Cross-linking can be achieved by incorporating monomers of e.g. N-methylol acrylamide, N-(iso-butoxymethylene)acrylamide, methyl acrylamidoglycolate methyl ether (all 0.5-5%) or metal chelates, e.g., acetylacetonates of Zr, Al, or Fe (up to 2% of polymer weight) into the polymer backbone which then cross-links during drying after spreading on a substrate.

Al and Ti acetylacetonates and similar compounds can also be added after the polymerization step in concentrations between 0.1 and 3% of the polymer weight and used as an internal cross-linker through utilizing carboxylic groups in the polymer backbone during the drying step.

Multi-functional isocyanates like TMDI, hexamethylene diisocyante, can be used to chemically inter link hydroxylic or carboxylic functions of different polymer chains, added in concentrations up to 5%, for example 1%, of the polymer weight.

Internal cross-linking can also be achieved between the carboxylic groups in the polymer backbone and added amino resins such as melamine, benzoguanamine, glycoluril, urea derivatives e.g. hexamethoxymethyl melamine, methoxymethyl methylol melamine, methoxymethyl ethoxymethyl benzoguanamine, tetrabutoxymethyl glycoluril, butoxymethyl methylol urea (up to 6%).

The above mentioned cross-linking can also be achieved using polycarbodiimides or multifunctional propylene imines.

The backbone adhesive polymer used as the adhesive component of the composition must include a functional group that is able to react chemically or physico-chemically with the internal cross-linker. It is also possible to use, as the starting or base adhesive, one which is manufactured with bound-in curable molecules; this is mixed with further curable molecules (not bound-in). The mechanism of internal cross-linking must not be a free radical mechanism because that is the mechanism used for effecting cross-linking for the switching.

Preferably, the curable molecules and the adhesive are soluble in each other when in the dry state, i.e., in the absence of a solvent. Alternatively, in the case that the adhesive and the curable molecules are not mutually soluble in each other when dry, or are only partly mutually soluble, they are uniformly dispersed in the composition. Typically, the adhesive (or the base adhesive if a mixture of adhesives is used) will be selected from polyacrylates, polyurethanes and silicone adhesives.

In the broadest sense, any conventional known unsaturated compounds could be used as the curable molecules, but preferred examples, used alone or in mixtures, are curable molecules such as acrylic acid esters or methacrylic acid esters of alcohols, glycols, pentaerythritol, trimethylpropane, glycerol, aliphatic epoxides, aromatic epoxides including bisphenol A epoxides, aliphatic urethanes, silicones, polyesters and polyethers, as well as ethoxylated or propoxylated species thereof.

The curable molecules have more than one unsaturated site, i.e., greater than single functionality. Multiple functionalities of 3 or greater, or more preferably 4 or greater are especially effective because curable molecules of this type are able to form highly cross-linked three-dimensional polymeric networks which are an important feature of switching, as will be explained below. Also, many curable molecules having multiple functionalities are commonly available at reasonable cost.

The radical initiator may be any species which is capable of producing radical species under the desired conditions but preferred examples are photoinitiators able to start the radical reaction under mild conditions, e.g. visible light, in order to promote radical polymerization reactions in the curable molecules. As a consequence, when the photoinitiator becomes activated by exposure to visible light, the curable molecules form chemical bonds with other curable molecules and hence create polymeric cross-linking. The effect of such cross-linking is to build a three-dimensional polymeric network entangling the adhesive polymer chains, thereby reducing their mobility and free volume. The photoinitiator may alternatively produce radical species under the mild conditions of long wave UV.

Curable molecules having multiple functionality are able to form highly cross-linked three-dimensional polymeric networks easily and hence exhibit good switching properties. The adhesive strength of the adhesive becomes reduced and it becomes less tacky so that it may be peeled more easily from the surface to which it is attached.

The adhesive mixture preferably also contains stabilizers which are added in order to prevent spontaneous cross-linking of the curable molecules during storage. Examples of such stabilizers are hydroquinones such as 4-methoxy phenol (sometimes referred to as hydroquinone monomethyl ether) and 2,4-ditert-butyl-methoxyphenol, or 1-piperidinyloxy-4,4'-[1,10-dioxo-1,10-decanediyl)bis(oxy)]bis[2,2,6,6-tetra methyl] and pentaerythritol tetrakis(3-(3,5-di-tert-butyl-4-hydroxyphenyl)propionate).

The adhesive mixture may also include photo-sensitisers. Since a sensitising species often absorbs energy in a different part of the spectrum from the initiator, more effective use of the light source may be achievable through the incorporation of sensitisers into the mixture. Many photo-sensitisers are complex organic molecules, absorbing in the visible portion of the spectrum.

The adhesive mixture may also incorporate light scattering particles to increase the effect of irradiation of the adhesive mixture. Preferably, the light scattering particles are an inorganic compound such as silica powder, alumina powder, silica-alumina powder or mica powder with particle sizes of the order of 10 nm or greater, typically up to 1 µm.

Any conventionally known free radical initiators may be used. Particularly preferred are those initiators which react to visible light radiation, although initiators which react under shorter wavelength light may be used in the compositions, depending on the application. Thus, free radical initiators which may be mentioned include titanocene photoinitiators; dye/co-initiator systems, e.g., thionine/triethanol-amine; dye/borate salt systems; dye/peroxide systems and 1,2-diketone/co-initiator systems, e.g., camphor-quinone/tertiary amine.

Examples of visible light photoinitiators (which include Irgacure 784 because it absorbs light both in the UV and visible spectrum) are: Benzildimethyl ketal; Phenanthrenequinone; Titanocenes (of which Irgacure 784 is one example); Bis(2,4,6-trimethyl-benzoyl)-phenylphosphineoxide.

Examples of UV photoinitiators are: Benzoin and ethyl, isopropyl or isobutyl ethers of Benzoin; Benzophenone and hydroxy or methyl benzophenones; 2-Methyl-1[4-(methylthio)phenyl]-2-morpholinopropan-1-one; Acetophenone and 4'-Phenoxyacetophenone; Benzoyl-biphenyl; Benzil; Anisoin, as well as the Irgacures such as Irgacure 651 (benzyl dimethyl ketal) or Irgacure 907 (2-methyl-1-[4-(methylthio)phenyl]-2-morpholino-propan-1-one); or the Uvatones, such as Uvatone 8302 (2,2-diethoxy-1,2-diphenyl ethanone).

Preferred free radical photoinitiators for medical applications are the titanocene initiators such as bis(.eta.5-cyclopentadienyl)-bis(2,6-difluoro-3-[pyrrol-1-yl]-phenyl) titanium, sold in the UK by Ciba Geigy as Irgacure 784 (Trade Mark).

In embodiments, the second absorbent adhesive composition comprises a polymer comprising monomer units selected from the group consisting of styrene, isoprene, butadiene, ethylene, and butylene.

In embodiments, the second absorbent adhesive composition comprises a styrene block co-polymer.

In embodiments, the second absorbent adhesive composition comprises a styrene block co-polymer selected from the group consisting of styrene-isoprene-styrene (SIS), styrene-butadiene-styrene (SBS), styrene-isobutylene-styrene (SIBS), and styrene-ethylene/butylene-styrene (SEBS).

In embodiments, the second absorbent adhesive composition comprises a polyethylene copolymer.

In embodiments, the second absorbent adhesive composition comprises a polyethylene copolymer selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

In embodiments, the second absorbent adhesive composition comprises polyisobutylene (PIB).

In embodiments, the absorbent adhesive composition may be switchable as described herein for the switchable adhesive composition.

In embodiments, the second absorbent adhesive composition comprises absorbent material. In embodiments, the second absorbent adhesive composition comprises water absorbent material.

In embodiments, the second absorbent adhesive composition comprises absorbent material selected from the group consisting of hydrocolloids, microcolloids, salt, and super absorbent particles.

In embodiments, the absorbent adhesive composition comprises an absorbent material in an amount of 1-60% (w/w) of the composition.

For instance, the absorbent adhesive composition comprises an absorbent material in an amount of 1-40% (w/w) or 1-20% (w/w) or 20-40% (w/w) or 20-60% (w/w) or 40-60% (w/w) or 25-50% (w/w) of the composition.

In embodiments, the absorbent material is selected from hydrocolloid, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, bentone, bentonite, and mixtures thereof.

In embodiments, the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

In embodiments, the water soluble salt is selected from $NaCl$, $CaCl_2$, $K_2SO_4$, $NaHCO_3$, $Na_2CO_3$, $KCl$, $NaBr$, $NaI$, $KI$, $NH_4Cl$, $AlCl_3$, $CH_3COONa$, $CH_3COOK$, $HCOONa$, $HCOOK$, and mixtures thereof.

In embodiments, the switchable and/or the absorbent adhesive composition may comprise ingredients such as tackifiers, extenders, non-reactive polymers, oils (e.g. polypropyleneoxide, ethyleneoxide-propyleneoxide copolymers, mineral oil), plasticizers, fillers, and surfactants.

In embodiments, the absorbent adhesive composition has an absorption of at least $0.05$ $g/cm^3/2$ h, measured as described herein, such as an absorption of at least 0.06, 0.07, 0.08, 0.09, 0.1, 0.2, 0.3, 0.4, 0.5, 0.6, 0.7, 0.8, 0.9, or 1 $g/cm^3/2$ h measured as described herein.

In embodiments, the first switchable adhesive composition and/or the second absorbent adhesive composition has a moisture vapor transmission rate (MVTR) above 250 $g/m^2/24$ h measured as described herein, such as above 500, 750, 1000, 1250, 1500, 2000, 2500, or 3000 $g/m^2/24$ h measured as described herein.

Moisture vapour transmission rate Moisture vapour transmission rate (MVTR) is measured in grams per square meter $(g/m^2)$ over a 24 hours period using an inverted cup method.

A container or cup that was water and water vapour impermeable having an opening of 035 mm was used. 20 mL saline water (0.9% NaCl in demineralised water) was placed in the container and the opening was sealed with the test adhesive mounted on a highly permeable polyurethane (PU) backing film (BL9601 foil from Intellicoat). The container was placed into an electrically heated humidity cabinet and the container or cup was placed upside down, such that the water was in contact with the adhesive. The cabinet was maintained at 32° C. and 15% relative humidity (RH).

The weight loss of the container was followed as a function of time. The weight loss was due to water transmitted through the adhesive and/or film. This difference was used to calculate the MVTR of the test adhesive film. MVTR was calculated as the weight loss per time divided by the area of the opening in the cup (g/m²/24 h).

The MVTR of a material is a linear function of the thickness of the material. Thus, when reporting MVTR to characterize a material, it is important to inform the thickness of the material which MVTR was reported. We used 150 µm as a reference. If thinner or thicker samples were measured, the MVTR was reported as corresponding to a 150 µm sample. Thus a 300 µm sample with a measured MVTR of 10 g/m²/24 h was reported as having MVTR=20 g/m²/24 h for a 150 µm sample because of the linear connection between thickness of sample and MVTR of sample.

Finally, we noted that by using this method, we introduced an error by using a supporting PU film. Utilizing the fact that the adhesive/film laminate was a system of two resistances in series eliminated the error. When the film and the adhesive are homogeneous, the transmission rate may be expressed as:

$$1/P(\text{measured}) = 1/P(\text{film}) + 1/P(\text{adhesive}).$$

Hence, by knowing the film permeability and thickness of the adhesive, it was possible to calculate the true permeability of the adhesive, P(adhesive), using the following expression:

$$P(\text{adhesive}) = d(\text{adhesive})/150 \text{ µm} * 1/(1/P(\text{measured}) - 1/P(\text{film}))$$

where d(adhesive) was the actual measured thickness of the adhesive and P(film) was the MVTR of the film without any adhesive on and P(measured) was the actual measured MVTR.

Moisture Absorption

Samples were prepared by thermoforming to a 0.5 mm thick adhesive film between two release liners. With a punching tool, samples were punched out. Sample size was 25×25 mm. The release liners were removed. The samples were glued to an object glass and placed in a beaker with physiological salt water and placed in an incubator at 37° C.

The sample was weighed at the outset (M(start)) and after 2 hours (M(2 hours)). Before weighing, the object glass was dried off with a cloth. For a 25×25 mm sample the area was 6.25 cm² (the surface edges were left out of the area). The moisture absorption may be calculated as: Water absorption after 2 hours=(M(2 hours)–M(start))/6.25 cm². The result is in the unit g/cm² per 2 hours.

Peel Force

Following the quantities and steps of a recipe, the compounds are hand mixed in a dark glass recipient for 1-2 minutes. The mixtures are let to rest for 24 h before use, the necessary time for the cross-linker to dissolve.

Afterwards the solution is coated with a dog-bone coater (f ex. using the 500 µm thickness), on a siliconized paper used as a release liner (RL). Before use, or before addition of top film (that can be polyurethane PU or polyethylene PE), the films are let for evaporation for a long enough time (48-72 h). The final thickness of the samples varies between 120 and 170 µm.

When HC were added the same coating procedure is applied, only the thickness of the films will be different.

To perform peel tests 90°, the samples with top film added (PU or PE) were cut in rectangular shapes (25×100 mm) and a helping tape on top. For the uncured samples, an occlusive black film was added on top to protect them from curing; also fast and in-the-dark handling was performed.

A sample of 25×100 mm2 was cut from the adhesive and firmly pressed on to a thoroughly cleaned plate (HDPE or TEFLON). A 25×300 mm2 piece of auxiliary tape was then placed on the top of the adhesive and the whole sample pressure rolled to assure firm adhesion between the tape and the adhesive to be tested. After conditioning for 30 minutes at 23 plus or minus 3 degrees centigrade, the sample was mounted in a tensile testing machine and a 90 degrees peel test was carried out at a speed of 304 mm/min.

DETAILED DESCRIPTION OF THE DRAWINGS

Figure 1:
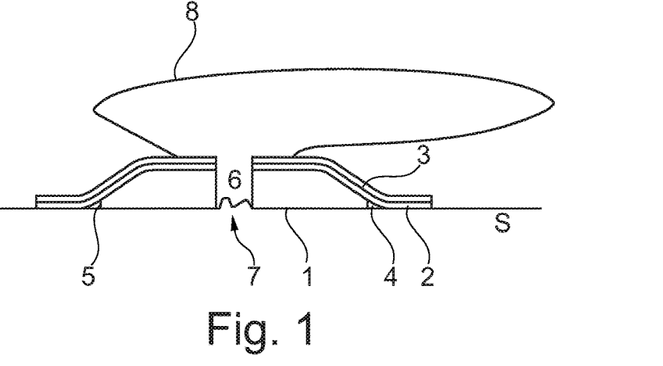
In FIG. 1 is shown schematically in cross section view an adhesive wafer with a bevelled second adhesive.
Figure 2:
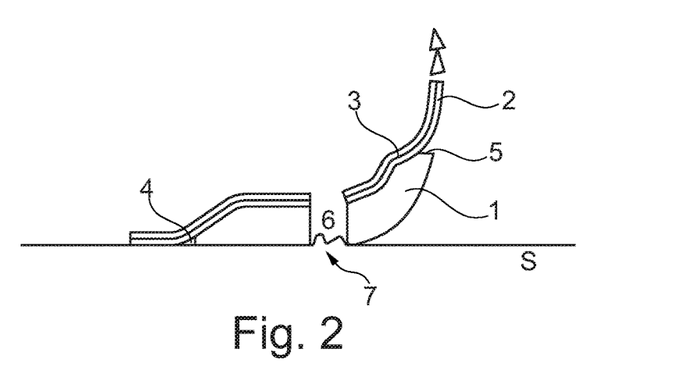
In FIG. 2 is shown schematically in cross section view an adhesive wafer where detachment from the skin is initiated.

FIG. 1 is a schematic cross-section view of an adhesive wafer. In this figure, a first adhesive layer 2, provided on a backing layer 3 is overlying a second adhesive 1. The lower surface of the adhesive wafer is the surface that is in contact with the skin S of the user during use. This surface may be covered by a release liner (not illustrated), which is removed prior to adhering the wafer to the skin S. In FIG. 1, the lower surface of the adhesive wafer is constituted by the second adhesive 1 covering the central portion of the surface and a first adhesive 2 at a peripheral portion along the outer edge. The upper surface is the surface facing away from the skin during use. This surface can be covered by a backing layer 3 to which a collecting bag 8 is or can be attached. The adhesive wafer has a centrally located through-going hole 6 allowing output from the stoma 7 to pass into the collecting bag 8. The second adhesive 1 is placed in the central part of the adhesive wafer, bordering the stoma 7 during use. The first adhesive 2 can be a switchable adhesive composition as described herein. The second adhesive 1 can be an absorbent adhesive composition as described herein. The second adhesive 1 is bevelled along its outer periphery, so the thickness of the central portion (the first thickness) of the second adhesive is larger than the thickness of the peripheral portion (the second thickness) of the second adhesive 5. In this way, the space volume 4, defined by the skin S, the first 2 and the second adhesive 1 is reduced or even eliminated as shown in FIG. 2. The first adhesive 2 will adhere both to the distal surface of the second adhesive 1 as well as to the sloping edge portion. Theoretically, the second thickness could be close to zero, but for practical reasons it is desired to have a rim portion 5 being substantially perpendicular to the plane of the adhesive layer, this perpendicular rim portion defining the second thickness. The second thickness 5 defines the size of the space volume 4 and the risk of delamination when peeling from skin S.

FIG. 2 is a schematic cross-section view of an adhesive wafer during detachment from the skin S. The skin S is here schematic shown as a straight line, but dependant of the strength of the adhesive as well as the softness of the skin, it may in real life be pulled up a little before detaching from the adhesive when the wafer is pulled away from the skin. When the wafer is detached at the edge portion and pulled away from the skin (as shown with arrow on FIG. 2), first the first adhesive will gradually detach from the skin, and after the space volume, the second adhesive begins to detach.

Embodiments, and features of the various exemplary embodiments described in this application, may be combined with each other ("mixed and matched"), unless specifically noted otherwise.

EXAMPLES

Example 1

In order to test the differences in peel between peel from a stiff substrate versus peel from skin, the following test could be made:

A way of preparing a skin-like substrate could be the following:

Skin may differ in structure, dependent on for example age, gender and physical condition of the person. In order to provide comparable and reproducible results, an artificial skin for testing peel on skin is prepared. The artificial skin is in the form of a soft silicone layer, covered with a soft film, as prepared as described below.

A soft skin-like substrate is prepared in order to simulate the stretching of skin when a product is removed. Casting of a 2 component silicone (84 g of Silgel 612 A and 66 g of Silgel 612 B) is carried out so that a soft 8-10 mm thick sticky silicone block is formed. The block is cured for 1 hour at 70 degrees.

On top of the silicone is fixed a soft 30 μm Polyurethane film (PU, Scapa Bioflex 130), functioning as substrate for the tested adhesives.

For comparison, a stiff substrate is prepared by adhering the PU film (Scapa Bioflex 130) to a stiff HDPE plate with a standard acrylic double-sided adhesive (3M1522).

Figure 3:
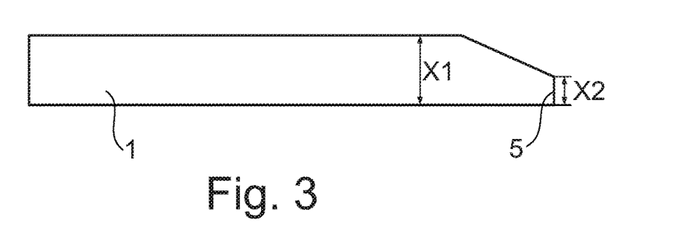
In FIG. 3 is shown a schematic cross-section view of the second adhesive layer.
Figure 4:
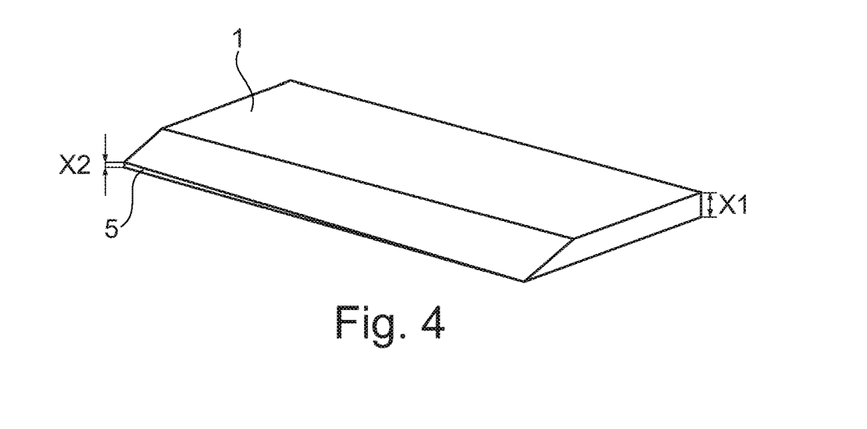
In FIG. 4 is shown schematically in perspective view a test sample of the second adhesive.

For preparing test samples the following method could be used:

The hydrocolloid adhesive could be as follows:

A standard wear adhesive for ostomy care (Kraton 1161, from Kraton polymers, Oppanol B12 from BASF. pectin LM CG, CP Kelco, Akucell AF288, Akzo Nobel, PB gelatine, PB Gelatins and Guar gum FG-20, Hercules Corp. is mixed in a z blade Austin 300 g mixer and applied vacuum) is pressed in to a 4 mm sheet. The sheet is bevelled from 4 mm to 0.05 mm over a distance of 11 mm giving an angle of bevelling of 20 degrees with the plane of the layer. The width of the bevelled edge is 80 mm. The bevelled edge is cut in such a way that the bevelled edge is 50 μm in one end and 800 μm in the other end. In that way a graded bevelling with different heights of bevelling from 3950 μm to 3200 μm is obtained. The increasing heights from 50 μm to 800 μm is used for determining when the hydrocolloid adhesive will come off together with the switched acrylic adhesive and when a delamination between the hydrocolloid adhesive and the switchable adhesive may occur during peeling from skin and from a stiff substrate. In FIG. 3 is shown a cross-section of the second adhesive layer, with the first thickness X1 of the central portion and the second thickness X2 of the edge portion. In FIG. 4 is shown the test sample of the second adhesive as described above.

The switchable adhesive could be as follows:

A BASF acResin A 260 UV with 1% photoinitiator is prepared by dissolving 80 g BASF acResin A 260 UV in 120 mL toluene at room temperature using a shaker with a speed of 30 rpm. 60 g of the resulting solution is mixed with 0.24 g Irgacure 784 photoinitiator using a spatula for 1 min. The switchable adhesive is provided in a layer of 60 μm thick and laminated to a 25 μm PU film and the laminate is placed over the bevelled and cut hydrocolloid adhesive to form the test object simulating the device according to the invention. The switchable adhesive laminate extend further than the bevelled edge hydrocolloid adhesive.

Testing of Delamination During Peeling of Adhesive from Substrate

Testing of the test object is carried out at 20 degrees at 50% humidity. The test object is placed on the soft substrate and pressed on to it with the finger to adhere. After 5 minutes, the switchable adhesive is switched with a 365 nm UVA light source for 15 sec. The switched adhesive is now only slightly adhesive and is peeled off with an angle of 90 degrees and a constant speed of approximately 1 cm/sec by hand (similar to the speed of normal removal of a ostomy product). The width (80 mm) of the graded bevelling front is peeled simultaneously. The height of the second thickness (X2) where the bevelled adhesives stop peeling off the substrate together with the switchable adhesive and instead delaminate is determined in μm by a Miotutoyo ocular. Three samples are tested. The expected results are shown in Table 1. As can be seen from the table, the samples does not delaminate when peeled from the stiff substrate, whereas samples with a low second height (X2) of the bevelled edge tends to delaminate when peeled from the soft substrate.

TABLE 1

| Sample | Peel substrate | Thickness before delamination, μm |
|---|---|---|
| 1 | Soft silicone with soft PU film | 300 |
| 2 | Soft silicone with soft PU film | 200 |
| 3 | Soft silicone with soft PU film | 150 |
| Average bevelling | | 217 |
| 5 | Stiff HDPE with soft PU film | +800 |
| 6 | Stiff HDPE with soft PU film | +800 |
| 7 | Stiff HDPE with soft PU film | +800 |
| Average bevelling | | +800 |

The results of the test from Table 1 show that the bevelled hydrocolloid adhesive will follow the switchable adhesive when tested on a stiff substrate. When tested on a skin-like soft substrate, delamination is much more inclined to occur.

The invention claimed is:

1. An ostomy device providing a hole adapted for placement around a stoma of a user, the ostomy device comprising:
    an adhesive wafer having a backing layer, a switchable adhesive layer applied to the backing layer, wherein the switchable adhesive layer is non-skin facing, and an absorbent adhesive layer applied to the switchable adhesive layer, where the backing layer defines a distal surface of the ostomy device and is adapted to receive a collecting bag for collection of output from the stoma;
    wherein the hole is sizable to receive a stoma and is formed through the backing layer, the absorbent adhesive layer, and the switchable adhesive layer;
    wherein the switchable adhesive layer is a ring-shaped annular band having a lateral extent that extends from an edge of the hole to an outermost perimeter of the ostomy device and the absorbent adhesive layer is formed around an entirety of the hole and extends from the edge of the hole to a rim that is located a radial distance away from the edge of the hole, where the radial distance is less than the outermost perimeter of the ostomy device;
    wherein the switchable adhesive layer covers the entirety of the surface of the absorbent adhesive layer;

wherein the absorbent adhesive layer has a first thickness measured at the edge of the hole and a second thickness measured at the rim, and the first thickness is larger than the second thickness;

wherein the switchable adhesive layer comprises a photoinitiator reactive to visible light; and wherein the absorbent adhesive layer includes absorbent particles distributed throughout the absorbent adhesive layer.

2. The ostomy device of claim 1, wherein the rim of the absorbent adhesive layer is bevelled to taper in a radial direction.

3. The ostomy device of claim 1, wherein the second thickness of the absorbent adhesive layer is less than 300 µm.

4. The ostomy device of claim 1, wherein the switchable adhesive layer comprises a polymer selected from the group consisting of polyacrylates, polyurethanes, and polysilicones.

5. The ostomy device of claim 1, wherein the switchable adhesive layer comprises curable molecules selected from the group consisting of acrylic acid esters or methacrylic acid esters of alcohols, glycols, pentaerythritol, trimethylpropane, glycerol, aliphatic epoxides, aromatic epoxides including bisphenol A epoxides, aliphatic urethanes, silicones, polyesters and polyethers.

6. The ostomy device of claim 1, wherein the photoinitiator is selected from the group consisting of titanocene photoinitiators; dye/co-initiator systems including thionine/triethanolamine; dye/borate salt systems; dye/peroxide systems and 1,2-diketone/co-initiator systems, including camphor-quinone/tertiary amine.

7. The ostomy device of claim 1, wherein the absorbent adhesive layer comprises monomer units selected from the group consisting of styrene, isoprene, butadiene, ethylene, and butylene.

8. The ostomy device of claim 1, wherein the absorbent adhesive layer comprises a styrene block co-polymer.

9. The ostomy device of claim 1, wherein the absorbent adhesive layer comprises a styrene block co-polymer selected from the group consisting of styrene-isoprene-styrene (SIS), styrene-butadiene-styrene (SBS), styrene-isobutylene-styrene (SIBS), and styrene-ethylene/butylene-styrene (SEBS).

10. The ostomy device of claim 1, wherein the absorbent adhesive layer comprises a polyethylene copolymer.

11. The ostomy device of claim 1, wherein the absorbent adhesive layer comprises a polyethylene copolymer selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

12. The ostomy device of claim 1, wherein the absorbent adhesive layer comprises polyisobutylene (PIB).

13. The ostomy device of claim 1, wherein the absorbent particles are selected from the group consisting of hydrocolloids, microcolloids, salt, and super absorbent particles.

* * * * *

UNITED STATES PATENT AND TRADEMARK OFFICE
CERTIFICATE OF CORRECTION

PATENT NO. : 11,077,224 B2  
APPLICATION NO. : 15/547810  
DATED : August 3, 2021  
INVENTOR(S) : Stroebech et al.

It is certified that error appears in the above-identified patent and that said Letters Patent is hereby corrected as shown below:

In the Specification

In Column 4, Line 52, delete "form" and insert -- from --, therefor.

In Column 14, Lines 50-52, delete "Moisture vapour transmission rate Moisture vapour transmission rate (MVTR) is measured in grams per square meter (g/m²) over a 24 hours period using an inverted cup method." and insert -- Moisture vapour transmission rate (MVTR) is measured in grams per square meter (g/m²) over a 24 hours period using an inverted cup method. -- at Line 51 as a new paragraph.

In Column 14, Line 54, delete "035 mm" and insert -- Ø35 mm --, therefor.

In Column 17, Line 33, delete "BASF." and insert -- BASF, --, therefor.

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*